United States Patent [19]

Roberts et al.

[11] Patent Number: 5,840,923
[45] Date of Patent: Nov. 24, 1998

[54] CHIRAL CYCLOPENTENE DERIVATIVES AND THEIR PREPARATION

[75] Inventors: Stanley Michael Roberts, Kenton; Horacio F. Olivo, Exeter; Raymond McCague, Miltin, all of Great Britain

[73] Assignee: Chiroscience Limited, Cambridge, Great Britain

[21] Appl. No.: 327,664

[22] Filed: Oct. 21, 1994

[30] Foreign Application Priority Data

Sep. 25, 1992 [GB] United Kingdom .................... 9220253
Nov. 1, 1993 [GB] United Kingdom .................... 9322502

[51] Int. Cl.⁶ .............................................. C07D 307/935
[52] U.S. Cl. ................................................. 549/311
[58] Field of Search ............................................... 549/311

[56] References Cited

FOREIGN PATENT DOCUMENTS

| 0 212 956 | 3/1987 | European Pat. Off. . |
| 0 267 878 | 5/1988 | European Pat. Off. . |
| 0 271 433 | 6/1988 | European Pat. Off. . |
| 0 501 310 | 9/1992 | European Pat. Off. . |
| WO 92/18444 | 10/1992 | WIPO . |

OTHER PUBLICATIONS

Grieco et al., "Total Synthesis of (±)–Sesbanimide A and B", Journal Of The Chemical Society, Chemical Communications, No. 4, pp. 368–370, published Feb. 15, 1992.

Lubineau et al., "Hetero Diels–Alder Reaction In Water. Synthesis of α–Hydroxy–γ–Lactones", Tetrahedron Letters, vol. 32, No. 51, pp. 7529–7530, published Dec. 16, 1991.

Saville–Stones et al., "Synthesis Of (±)–2'3'–Didehydro–2'3'–dideoxy Nucleosides via a Modified Prins Reaction And Palladium(o) Catalysed Coupling", J. Chem. Soc. Perkin Trans. 1, No. 10, pp. 2603–2604, published Oct. 1991.

Sustmann et al., "Thermolyse von Perestern mit Bicyclo [3.1.0]hexangeruest", Chemische Berichte, vol. 109, pp. 444–454, published 1976.

Mac Keith et al, "J. Chem. Soc. Perkin Trans. I," pp. 313–314, 1993.

*Primary Examiner*—Ba K. Trinh
*Attorney, Agent, or Firm*—Foley & Lardner

[57] ABSTRACT

An optically-purified enantiomer of the lactone 4-hydroxy-2-oxabicyclo-[3.3.0]oct-7-en-3-one or an acylate thereof can be obtained by biotransformation. It is a useful synthon in the preparation of an enantiomer of 3-hydroxymethyl-2-hydroxycyclopentene that can be used to prepare carbocyclic nucleosides as a desired enantiomer.

7 Claims, No Drawings

CHIRAL CYCLOPENTENE DERIVATIVES AND THEIR PREPARATION

FIELD OF THE INVENTION

This invention relates to chiral cyclopentene derivatives and also to their preparation and use. In single enantiomer form, hydroxylated cyclopentene derivatives are valuable precursors to carbocyclic nucleosides and to cholesterol-lowering agents.

BACKGROUND OF THE INVENTION

WO-A-9218444 (published Oct. 29, 1992) and commonly-assigned Application Ser. No. 08/211,623, describe such enantiomers, of 2-hydroxymethyl-4-hydroxycyclopentene, and their synthesis. The first synthetic step is a Prins addition reaction of formaldehyde and formic acid onto cyclopentadiene. The adduct is a mixture of isomers which are separated chromatographically as appropriately protected derivatives and resolved in enzyme-mediated transformations.

The sate reaction is described by Sackville-Stones et al, JCS Perkin Trans. I (1991) 2603. Enantiomers of 3-hydroxymethyl-2-hydroxycyclopentene are described as a minor product. The chiral cyclopentene derivatives are useful as synthons in the preparation of carbocyclic nucleosides such as Carbovir. However, a difficulty with this methodology is the problematic requirement for separation of regioisomers and diastereoisomers in addition to the enantiomers.

Lubineau et al, Tet. Lett. 32(51):7529–30 (1991), describe the hetero-Diels-Alder reaction of cyclopentadiene with glyoxylic acid, to give an α-hydroxy-γlactone, specifically 4-hydroxy-2-oxabicyclo[3.3.0 ]oct-7-en-3-one. This adduct has been used, as a mixture of diastereoisomers, in the synthesis of (±)-sesbanimides; see Grieco et al, JCS Chem. Commun. (1992) 368.

SUMMARY OF THE INVENTION

The present invention is based on the discovery that the known lactone (which is produced from starting materials that are cheap and readily-available) can be resolved by biotransformation and that the resultant enantiomer can be used to produce the known hydroxylated cyclopentene derivatives in enantiomeric form, i.e. ready for use as a synthon in the preparation of a desired enantiomer of Carbovir or other carbocyclic nucleosides.

DESCRIPTION OF THE INVENTION

As indicated above, the adduct of cyclopentadiene and glyoxylic acid has previously been produced as a racemate. The present invention provides methods for its transformation into single or at least substantially pure (e.g. more than 50% ee) enantiomer material of greater utility.

In one aspect of the invention, the adduct (which is a mixture of diastercoisomers owing to the configuration of the secondary hydroxyl fraction) is resolved to give a desired enantiomer. The adduct may be recrystallised to provide a single diastereoisomer that is the major component of the original mixture, but this is often unnecessary.

One resolution procedure comprises treatment with an acyl donor (e.g. vinyl acetate) and a suitable biocatalyst in an appropriate solvent (e.g. heptane). The biocatalyst may be a lipase such as *Pseudomonas fluorescens* (pfl), *P. lipoprotein* or *Candida cylindracea* lipase.

Alternatively, resolution may be conducted by acylation (e.g. with butyric acid) then hydrolysis with a suitable biocatalyst in an aqueous system. The butyrate is transformed at substantially the same rate as the acetate, although the aqueous biotransformation of the butyrate is faster than the esterification with vinyl acetate. In general, it is preferred that the acylate has up to 6 C atoms.

The transformation leaves one enantiomer as the secondary alcohol and the other as its acyl derivative. They may be separated by conventional methods. If the biocatalyst preferentially transforms the endo rather than exo adduct, as is the case for pfl, the endo diastereoisomer being the major component and the fact that endo-hydroxy-lactone can be recrystallised from exo in the optically-active product means that it is unnecessary to recover pure endo-racemate.

As the second feature of the invention, resolution of the adduct as the single diastereoisomer or a mixture of the two, is by means of a biocatalyst in aqueous medium that effects hydrolysis of the lactone function in a manner specific for one enantiomer. That leaves unconsumed lactone and ring-opened carboxylate that can be separated through solvent extraction.

Conversions of the resolved adduct into a synthetically useful diol, e.g. as described by Sackville-Stones et al, supra, may be accomplished by a sequence of standard chemical transformations. The reaction conditions for such transformations are illustrated in the Examples, below, and firstly with reference to Scheme 1, Exemplifying reagents and conditions for Scheme 1 are: (i) pfl, vinyl acetate; (ii) LiAlH$_4$, THF; (iii) NaIO$_4$, Et$_2$O—H$_2$O; (iv) NaBH$_4$, MeOH; (v) Ph$_3$CCl, Et$_3$N, Me$_2$NC$_5$H$_4$CH$_2$Cl$_2$; (vi) Ac$_2$O, pyridine; (vii) 2-amino-6-chloropurine, NAH, DMF, (Ph$_3$P)$_4$Pd, THF. The three operations of steps ii, iii and iv be conducted without purification of the intermediates. As an alternative to the given sequence of steps ii, iii and iv, the hydroxy-lactone may be reacted first with a carbanionic nucleophile such as RLi, to give a compound of formula IV (see claim 6; IV is a generalised version of 4). Effective dehydroxymethylation, to give 5, may be conducted using KIO$_4$ and NaBH$_4$.

Tritylation of the primary hydroxy group in the diol (–)-5 gives (–)-6 and acetylation of the secondary hydroxy group gives the ester (–)-7 [α]$^{25}_D$ –85 (c 1.0, CHCl$_3$). Compounds of type 7 are excellent precursors of 2',3'-dideoxydidehydrocarbocyclic nucleosides through the use of Trost-style organopalladium chemistry. Thus, reaction of the allylic acetate (–)-7 with $^2$-amino-6-chloropurine and sodium hydride in the presence of tetrakis(triphenylphosphine)palladia(O) gives the cyclopentene derivative (–)-8 [α]$^{25}_D$ –75 (c 1.0, CHCl$_3$), a known precursor of the anti-HIV agent Carbovir (–)-9. Interest in this anti-viral substance remains at a high level. The appropriate preparation of Carbovir is described by Evans et al, JCS Perkin I (1992) 589; see also Sackville-Stones et al, supra; the contents of both these documents is herein incorporated by reference.

Another aspect of this invention lies in transforming the hydroxylactone to the dial (5), using an efficient one-solvent system for the three process steps. Included in these three steps is a lithium aluminium hydride reduction, a sodium periodate oxidative cleavage and finally a sodium borohydride reduction. The intermediates in this reaction sequence, which are not isolated, are the triol (4) and the aldehyde (4a). Reference is made to Scheme 2, below.

The process is applicable to either enantiomer of compound (1 or 2), or its racemate, since none of the process steps involves epimerisation of either stereogenic centre.

With further reference to Scheme 2, the cis relationship of the two stereogenic centres is by virtue of a Dials-Alder reaction between glyoxylic acid and cyclopentadiene followed by rearrangement to compound (1). It can be assumed that the chiral integrity of the product, compound (5) will be directly related to the starting material.

In the process described herein the lithium aluminium hydride reduction is carried out in refluxing tetrahydrofuran (THF). Hydrolysis of the excess reducing agent and the lithiated organic material is achieved with a 20 vol % addition of water and filtering the solids with Celite. The filter cake must be washed with at least two aliquots of 20 vol % water in THF. The triol (4) is slightly unstable if warmed and freed of solvent. It is fortunate that the triol can be oxidatively cleaved by the addition of solid sodium periodate to the triol, e.g. in 10 vol % water in THF.

The various iodate salts can be easily filtered upon reaction completion. The aldehyde solution is very unstable and is thus reduced to the much more stable product (5). This is achieved simply by the addition of solid sodium borohydride to a chilled solution of compound (4a) in 10% water in THF. The facility for converting monophasic aqueous THF to a biphasic mixture simply by the addition of solid sodium chloride to aqueous saturation works very well in this process. The product/THF solution can be dried and concentrated and the saturated aqueous phase extracted further with THF.

Product purification is via concentration and final is fractional distillation under high vacuum.

The invention is now further illustrated by way of reference to the following Examples.

EXAMPLE 1

Cyclopentadiene (240 cm$^3$, 2.87 mol), aq. glyoxylic acid (225 cm$^3$, 50% w/v solution, 2.01 mol) and water (800 cm$^3$) were vigorously stirred at 0° C. to room temperature for 4 days. The solution was extracted with heptane (4×250 cm$^3$), to remove unchanged cyclopentadiene, saturated with sodium chloride and further extracted with ethyl acetate (12×500 cm$^3$). The combined organic layers were concentrated to 1.5 dm$^3$, cooled to 0° C. and washed with cold saturated aqueous sodium hydrogen carbonate (2×200 cm$^3$), to remove unchanged glyoxylic acid. The aqueous solution was extracted with ethyl acetate (3×500 cm$^3$). The combined organic layers were dried (Na$_2$SO$_4$), filtered and evaporated to give the lactones (±)-1 and (±)-2 as a yellow mobile oil which crystallised on storage (ca. 65% yield). NMR spectroscopy showed the ratio 1:2 was 4:1. The crude product was, triturated with methyl tert-butyl ether to remove the oily lactone (±)-2, and the lactone (±)-1 (88 g, 628 mol) was isolated as a sand-coloured crystalline solid (greater than 95% pure by NMR spectroscopy) which could be used in the next step. Recrystallisation from diethyl ether gave pure (±)-4-hydroxy-2-oxabicyclo[3.3.0]oct-7-en-3-one 1.

Alternatively, chromatography of the crude product over silica using hexane in ethyl acetate (ratio 2:3) as eluant to give, in the first fractions, the lactone (±)-2; $v_{max}$/cm$^{-1}$ 3427, 1764, 1615, 1184, 1116 and 986; $\delta_H$(CDCl$_3$) 6.1 (1 H, m, 7-H or 8-H), 5.9 (1 H, m, 8-H or 7-H), 5.55 (1 H, m, 1-H), 4.15 (1 H, d, J 7, 4-H). 3.5 (1 H, br, s, OH) and 3.05–2.55 (3 H, m, 5-H and 2×6-H); $\partial_c$(CDCl$_3$) 178.2, 136.9, 129.2, 87.5, 74.3, 44.3 and 36.6. Later fractions contained the lactone (±)-1 m.p. 68°–69° C.; $v_{max}$/cm$^{-1}$ 3443, 3023, 1765, 1615 and 1134; $\delta_H$(CDCl$_3$) 6.33 (1 H, m, 7-H or 8-H), 5.93 (1 H, m, 8-H or 7-H), 5.33 (1 H1, dt, J 6,2, 1-H), 4.72 (1 H, d, J 9, 4-H), 3.5 (1 H. br, s, OH) and 3.21–2.45 (3 H, m, 5-H and 2×6-H); $\delta_c$(CDCl$_3$) 177.6, 140.9, 127.4, 86.4, 67.0, 40.4 and 30.7 (Found: C, 59.9; H, 5.7. C$_7$H$_8$O$_3$ requires C, 60. 0; H 5.75%).

The hydroxy-lactones 1 and 2 are thus produced in the ratio 4:1 on a large scale (10–250 g) (crude yield ca. 65%). The compounds were separated by chromatography over silica and the disposition of 4-OH in the epimers was elucidated by NMR spectroscopy. The epimer 1 crystallises from the crude product. The minor component 2 can then be removed by trituration whereupon 1 can be obtained in greater than 95% purity in 31% yield. Recrystallisation from diethyl ether gave pure 1. Confirmation of the proposed structure for the lactone 1 was obtained by X-ray crystallography.

EXAMPLE 2

This Example illustrates hydrolysis of the butyrate of the hydroxy-lactone-(±) -4-hydroxy-2-oxabicyclo[3.3.0] oct-7-en-3-one.

The (±)-hydroxy-lactone ester (2.391 kg, 4.5:1 ratio of endo:exo isomers) was stirred in phosphate buffer (20 L, 0.1M KH$_2$PO$_4$) at 25° C., and the pH adjusted to 6.6 using 10M NaOH. Lipase (Amano PS, 120 g) was added as a slurry in IL phosphate buffer, then the mixture stirred well to disperse the ester. The mixture was controlled at pH 6.6 by automatic addition of 10M NaOH. After addition of 4.85 mol hydroxide, 10% w/v NaCl was added, then excess butyrate ester and undissolved solids were removed by centrifugation. The supernatant was extracted 3 times with an equal volume of ethyl acetate, the organic extracts dried (MgSO$_4$), then concentrated under reduced pressure to 5% of the original volume. Methyl tert-butyl ether was added to induce crystallisation and after chilling to 5° C., the crystals were harvested by filtration, then recrystallised from dichloromethane, yielding 396 g (−) -hydroxy-lactone of >99% ee. The ee was determined as the p-toluate ester, separating enantiomers on a 25 cm Pirkle L-leucine column (4% ethanol in heptane as mobile phase, 254 nm, 2 ml/min).

EXAMPLE 3

This Example illustrates esterification of (±)-hydroxy-lactone in vinyl acetate.

Vinyl acetate (2 L), (±)-hydroxy-lactone (100 g), and lipase (28 g, Amano PS) were stirred gently at 40° C. for 72 hours. The enzyme was recovered by filtration, then the vinyl acetate evaporated under reduced pressure. Methyl tert-butyl ether (250 ml) was added to cause crystallisation of (+) -hydroxy-lactone. This was recovered by filtration, yielding 19 g (+)-hydroxy-lactone of >99% ee. The remaining lactone was partitioned away from the ester in 1:1 toluene:brine (600+600 ml) washing the organic layer twice with brine. The toluene layer was then dried (MgSO$_4$), and concentrated under reduced pressure, then MeOH (400 ml) and sodium methoxide (2 g) were added. After stirring for 1 h, acetic acid (2 ml) was added, and the nethanol evaporated, replacing with ethyl acetate (400 ml). The resulting suspension was filtered through silica gel, then concentrated, and crystallisation induced by addition of methyl tert-butyl ether. The crystals were recovered by filtration, and dried, yielding (−)-hydroxylactone (18 g) of 98ee.

The hydroxy-lactone 1 was thus resolved by an enzyme-catalysed process. In particular, the lactone (±)-1 was partially acetylated using *Pseudomonas fluorescens* lipase (pfl) in vinyl acetate.

EXAMPLE 4

The (−)-hydroxy-lactone derived from the biocatalytic hydrolysis was converted into the diol (−)-5 in three steps.

Thus, lithium aluminium hydride (1.4 g) was suspended in tetrahydrofuran (50 ml) and the mixture heated to reflux. The (−)-hydroxy-lactone (5.32 g) in tetrahydrofuran (50 ml) was then added over 20 min. The mixture was allowed to cool to ambient and quenched by the addition of saturated aqueous sodium sulphate solution (15 ml). The solid was removed by filtration and washed with tetrahydrofuran (5×10 ml). The combined filtrate and washings were concentrated under reduced pressure and the residual crude triol 4 taken up in 1:1 methyl tert-butyl ether: saturated brine (100 ml). This biphasic mixture was cooled to 0° C. and sodium periodate (8.52 g) added in portions over 10 min. The resulting mixture was stirred for 1 h, then the solids removed by filtration and washed with methyl tert-butyl ether (50 ml). The filtrates were concentrated under reduced pressure and the residue dissolved in ethanol (50 ml). The solution was cooled to 0° C. and sodium borohydride (1.41 g) added in small portions over 2 min. The resulting mixture was stirred at 0° C. overnight then sodium chloride added to saturate the aqueous layer which was extracted with ethyl acetate (3×100 ml). The organic layers were combined, dried over sodium sulphate and concentrated under reduced pressure to leave crude diol (−)-5 (3.27 g). Distillation at 1 mm Hg is used to purify the diol and generally gives a yield of about 35% from the (−)-hydroxy-lactone.

EXAMPLE 5

Lithium aluminium hydride (140 g, 3.69 mol) was suspended in tetrahydrofuran (0.05% water; 2.5 l) under a nitrogen atmosphere. The suspension was brought to reflux which was maintained for 0.25 hr. A solution of hydroxy-lactone (1) (500 g, 3.52 mol) in THF (2.5 l) was added steadily so as to maintain reflux without the application of heat to the vessel. The addition took 1.5 hr, at which point the reaction was complete.

Following cooling to ambient, water (1.2 l) was added carefully to the reaction mixture. When 0.5 l had been added, Celite (500 g) was then mixed with the semi-hydrolysed mixture, followed by addition of the remaining 0.7 l of water.

The mixture was filtered and the filter cake resuspended with 20% water in TBF (2 l), followed by filtration. This operation was repeated twice. All filtrates were combined, which amounted to some 10 l.

The triol (4) solutions 10 l containing 480 g, was cooled to 5° C. Sodium periodate (1 mol equiv. 690 g) was added portionwise over 3 hr. After a further 1.5 hr, the solid was filtered and washed with 10% water in THF (2 l).

The aqueous THF solution of aldehyde (4a; 12 l) was cooled to 5° C. Sodium borohydride was added carefully until all the aldehyde had been reduced. Approximately 50 g was required.

Sodium chloride (500 g) was added with vigorous stirring. After 0.5 hr, the phases were allowed to separate. The THF layer was removed and the aqueous phase extracted with 3×2 l of THF. The combined THF extracts were dried, filtered and concentrated to crude diol (5). The product was purified by fractional distillation at 0.6 m bar, and the fraction collected at 98°–102° C. boiling range. Yield: 52% pure from hydroxylactone (1) 214 g.

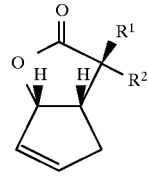

(±)-1 R¹ = H; R² = OH
(±)-2 R¹ = OH; R² = H

Scheme 1

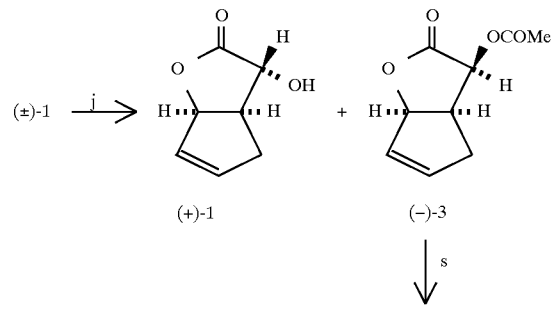

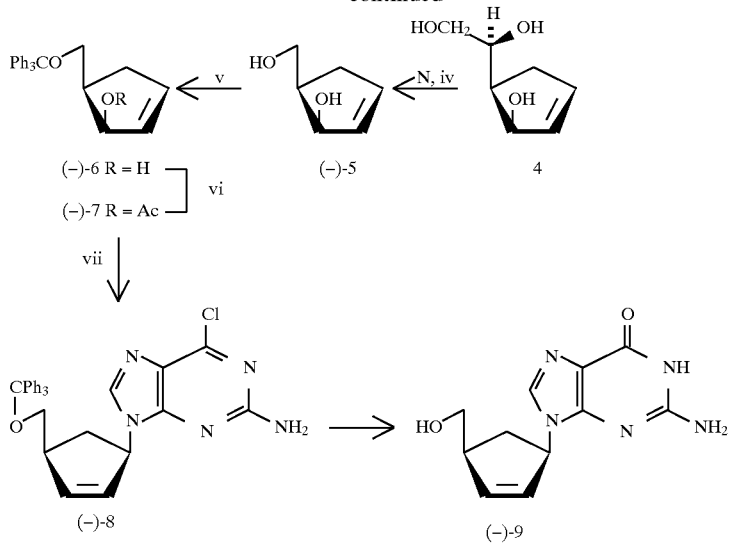

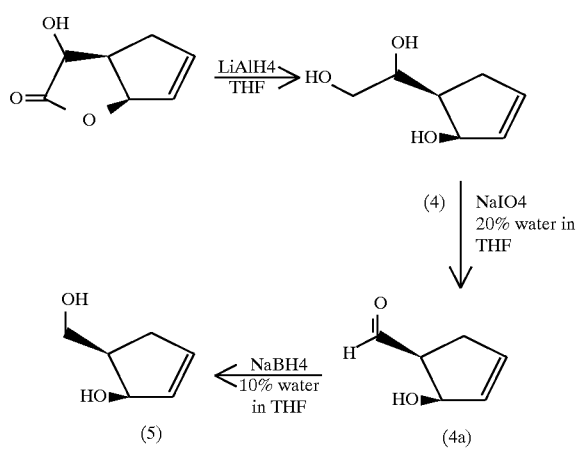

What is claimed is:

1. An enantiomer of the lactone 4-hydroxy-2-oxa-bicyclo[3.3.0]oct-7-ene-3-one or an acylate thereof, wherein the enantiomer is present in at least 50% enantiomeric excess with respect to the other enantiomer.

2. The enantiomer of claim 1, wherein the enantiomer is the (−)-enantiomer.

3. The enantiomer of claim 1, wherein the enantiomer is the (+)-enantiomer.

4. The enantiomer of claim 1, produced by a process comprising biocatalyst-mediated enantiospecific acylation of a racemic form of the lactone.

5. The enantiomer of claim 4, wherein the biocatalyst comprises a lipase.

6. The enantiomer of claim 1, produced by a process comprising biocatalytic enantiospecific hydrolysis of a racemic form of the acylate.

7. The enantiomer of claim 6, wherein the biocatalyst comprises a lipase.

* * * * *

UNITED STATES PATENT AND TRADEMARK OFFICE
CERTIFICATE OF CORRECTION

PATENT NO. : 5,840,923
DATED : November 24, 1998
INVENTOR(S) : Stanley Michael Roberts et al.

It is certified that error appears in the above-identified patent and that said Letters Patent is hereby corrected as shown below:

<u>Title page,</u>
Item [30] Foreign Application Priority Data, please insert -- PCT/GB92/00730, April 21, 1992, Great Britain --, and -- PCT/GB93/00826, April 21, 1993, Great Britain --.

Signed and Sealed this

Twenty-eighth Day of August, 2001

Attest:

NICHOLAS P. GODICI
Attesting Officer  Acting Director of the United States Patent and Trademark Office